US009575323B2

United States Patent
Fu et al.

(10) Patent No.: US 9,575,323 B2
(45) Date of Patent: Feb. 21, 2017

(54) BIOCHIP IMAGE-FORMING SYSTEM

(71) Applicant: NATIONAL PINGTUNG UNIVERSITY OF SCIENCE & TECHNOLOGY, Pingtung County (TW)

(72) Inventors: Lung-Ming Fu, Pingtung County (TW); Wei-Jhong Ju, Pingtung County (TW)

(73) Assignee: NATIONAL PINGTUNG UNIVERSITY OF SCIENCE & TECHNOLOGY, Pingtung (TW)

(*) Notice: Subject to any disclaimer, the term of this patent is extended or adjusted under 35 U.S.C. 154(b) by 0 days.

(21) Appl. No.: 14/970,430

(22) Filed: Dec. 15, 2015

(65) Prior Publication Data

US 2017/0010472 A1    Jan. 12, 2017

(30) Foreign Application Priority Data

Jul. 8, 2015 (TW) ............................. 104122190 A

(51) Int. Cl.
  *G02B 27/02* (2006.01)
  *G01N 21/86* (2006.01)
  (Continued)

(52) U.S. Cl.
  CPC ............. *G02B 27/025* (2013.01); *G01N 21/29* (2013.01); *G01N 21/78* (2013.01); *G02B 7/021* (2013.01);
  (Continued)

(58) Field of Classification Search
  CPC ..... G02B 7/021; G02B 27/025; G02B 27/028; G01N 21/78; G01N 21/86; G01N 21/29; G01N 2021/786; G01N 2201/0231; G07D 7/121; H01L 25/167; H01L 27/02; H01L 27/14618; H01L 27/14623; H01L 27/14625; H01L 27/1462
  (Continued)

(56) References Cited

U.S. PATENT DOCUMENTS

| 5,302,778 A * | 4/1994 | Maurinus | ............... H01L 25/167 174/521 |
| 6,661,084 B1 * | 12/2003 | Peterson | ............... H01L 25/105 257/680 |

(Continued)

FOREIGN PATENT DOCUMENTS

TW    I335429    1/2011

OTHER PUBLICATIONS

Wei-Jhong Ju et al., "Paper-Based Chip—Chip System for Fast Analysis of Albumin and Creatinine Levels in Serum", 2015 Kaohsiung International Instruments Show.

*Primary Examiner* — Loha Ben
(74) *Attorney, Agent, or Firm* — WPAT, P.C.; Anthony King

(57) ABSTRACT

The present invention provides a biochip image-forming system including a case having a cavity, an optical assembly, a chip-holding assembly and an electricity storage assembly. The cavity communicates with a chip inlet for a biochip to be inserted into the cavity through the chip inlet and an image outlet for an image of the biochip to be outputted from the cavity via the image outlet. The optical assembly is received in the cavity and aligned with the image outlet for forming the image of the biochip. The chip-holding assembly is received in the cavity and arranged between the optical assembly and a heating component. The chip-holding assembly aligns with the chip inlet for the biochip to be placed thereon. The electricity storage assembly is electrically connected with the optical assembly and the heating (Continued)

component. As such, a biochip can be analyzed conveniently using said biochip image-forming system.

20 Claims, 3 Drawing Sheets

(51) Int. Cl.
    *G01N 21/78* (2006.01)
    *G01N 21/29* (2006.01)
    *G02B 7/02* (2006.01)
    *H01L 25/16* (2006.01)
    *H01L 27/146* (2006.01)
    *H01L 31/0216* (2014.01)

(52) U.S. Cl.
    CPC ....... G02B 27/028 (2013.01); *G01N 2021/786* (2013.01); *G01N 2201/0231* (2013.01); *H01L 25/167* (2013.01); *H01L 27/14618* (2013.01); *H01L 31/02162* (2013.01)

(58) Field of Classification Search
USPC ...... 359/391, 798–801; 250/208.1, 215, 216, 250/370.09, 559.01, 559.05; 257/99, 431–433; 362/235, 543; 347/58; 174/521; 438/70
See application file for complete search history.

(56) References Cited

U.S. PATENT DOCUMENTS

| | | | |
|---|---|---|---|
| 6,811,079 B1 * | 11/2004 | Vraa | B41J 11/48 235/383 |
| 8,411,192 B2 * | 4/2013 | Fukamachi | G02B 7/021 348/335 |
| 2014/0268321 A1 * | 9/2014 | Damiano, Jr. | G02B 21/26 359/391 |

* cited by examiner

BIOCHIP IMAGE-FORMING SYSTEM

CROSS REFERENCE TO RELATED APPLICATIONS

The application claims the benefit of Taiwan application serial No. 104122190, filed on Jul. 8, 2015, and the subject matter of which is incorporated herein by reference.

BACKGROUND OF THE INVENTION

1. Field of the Invention

The present invention generally relates to an image-forming system and, more particularly, to a biochip image-forming system.

2. Description of the Related Art

As the wealth of society has gradually improved, "diseases of affluence," such as chronic diseases (e.g. diabetes and hypertension), are thus resulted. These diseases do not cause immediate death; however, they cannot be cured right away. Consequently, controlling progression of disease has become an important issue in patients' daily life.

For helping patients to manage disease progression, convenient medical devices are developed, such as sphygmomanometer, glucose meter and blood analyzer. With the development of bioengineering, biochip has been produced for fast genetic test or disease diagnosis. Proteins, nucleotides, antigens or antibodies of a testee can be dropped on a thumb-sized biochip, and can be analyzed using corresponding devices. An example of such biochip and analyzing device can be seen in Taiwan Patent No. 1335429.

However, the conventional analyzing device needs external magnetic force during analysis process, hence may not be suitable for a patient wearing a pacemaker. Besides, the conventional analyzing device has large size and cannot be easily carried, thus being inconvenient for patients to manage disease progression through biochips.

In light of the above, it is required to provide a solution which overcomes the above disadvantages and fulfills the needs of patients, thus improving its application convenience.

SUMMARY OF THE INVENTION

It is therefore the objective of this invention to provide a biochip image-forming system for assisting a user to analyze a specimen collected on a biochip without the limitations of time and place.

The present invention provides a biochip image-forming system including a case having a cavity, an optical assembly, a chip-holding assembly and an electricity storage assembly. The cavity communicates with a chip inlet for a biochip to be inserted into the cavity through the chip inlet and an image outlet for an image of the biochip to be outputted from the cavity via the image outlet. The optical assembly is received in the cavity and aligned with the image outlet for forming the image of the biochip. The chip-holding assembly is received in the cavity and arranged between the optical assembly and a heating component. The chip-holding assembly aligns with the chip inlet for the biochip to be placed thereon. The electricity storage assembly is electrically connected with the optical assembly and the heating component.

In a form shown, the optical assembly includes a lens assembly arranged between the image outlet and the chip-holding assembly and a backlight component fitted around the lens assembly for emitting light towards the chip-holding assembly.

In the form shown, the lens assembly includes a set of convex lenses having a magnifying power of 2× to 4× and a focal length of 1-2 cm.

In the form shown, the optical assembly includes a base. The base includes a lens-combining portion combined with the lens assembly and a backlight-positioning portion on which the backlight component is arranged.

In the form shown, the base includes an upper part and a lower part stacked with each other.

In the form shown, a magnet set is arranged between the upper and lower parts.

In the form shown, the lens assembly includes a magnetic member for combining the lens assembly to the lower part.

In the form shown, the lower part is covered by an opaque material.

In the form shown, the chip-holding assembly includes a chip-guiding layer having a groove extending inwards from an edge of the chip-guiding layer. The groove aligns with the chip inlet of the case.

In the form shown, the chip-holding assembly includes a shade layer arranged between the chip-guiding layer and the optical assembly. The shade layer includes an observing window aligned with the groove of the chip-guiding layer.

In the form shown, the chip-holding assembly includes a heat-conducting member arranged between the chip-guiding layer and the electricity storage assembly. The heat-conducting member includes a heater-combining portion for combining with the heating component.

In the form shown, the heat-conducting member includes a heat-conducting sheet and a supporting sheet. The heat-conducting sheet is arranged between the supporting sheet and the chip-guiding layer.

In the form shown, the heater-combining portion aligns with the groove of the chip-guiding layer.

In the form shown, the electricity storage assembly includes a rechargeable battery and a wireless induction component. The rechargeable battery is electrically connected with the backlight component and the heating component. The wireless induction component is coupled with the rechargeable battery.

In the form shown, the electricity storage assembly includes a backlight-driving component electrically connected with the rechargeable battery and the backlight component.

In the form shown, the case includes a lateral wall and two lids. The lateral wall includes two opposite openings communicated with the cavity. The chip inlet is arranged in the lateral wall between the two openings. The image outlet is arranged in one of the two lids. The two lids respectively cover the two openings.

In the form shown, the one of the two lids on which the image outlet is arranged is combined with the optical assembly. The other one of the two lids is combined with the electricity storage assembly.

In the form shown, the case includes a first supporting member and a second supporting member. The first supporting member is arranged between the optical assembly and the chip-holding assembly. The second supporting member is arranged between the chip-holding assembly and the other one of the two lids.

In the form shown, the first supporting member is in a form of a frame.

In the form shown, the first supporting member is covered by an opaque material.

The biochip image-forming system is provided with reduced volume and the reaction can be finished in a short time. Hence, the user can analyze the specimen collected on the biochip using the biochip image-forming system without the limitations of time and place. The biochip image-forming system meets the requirement for the patients to personally manage their disease progression, and overcomes the inconvenience due to particular time and place limitations of biochip analysis. Thus, the biochip image-forming system can be used in medical institutions and in home care.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

Figure 1:
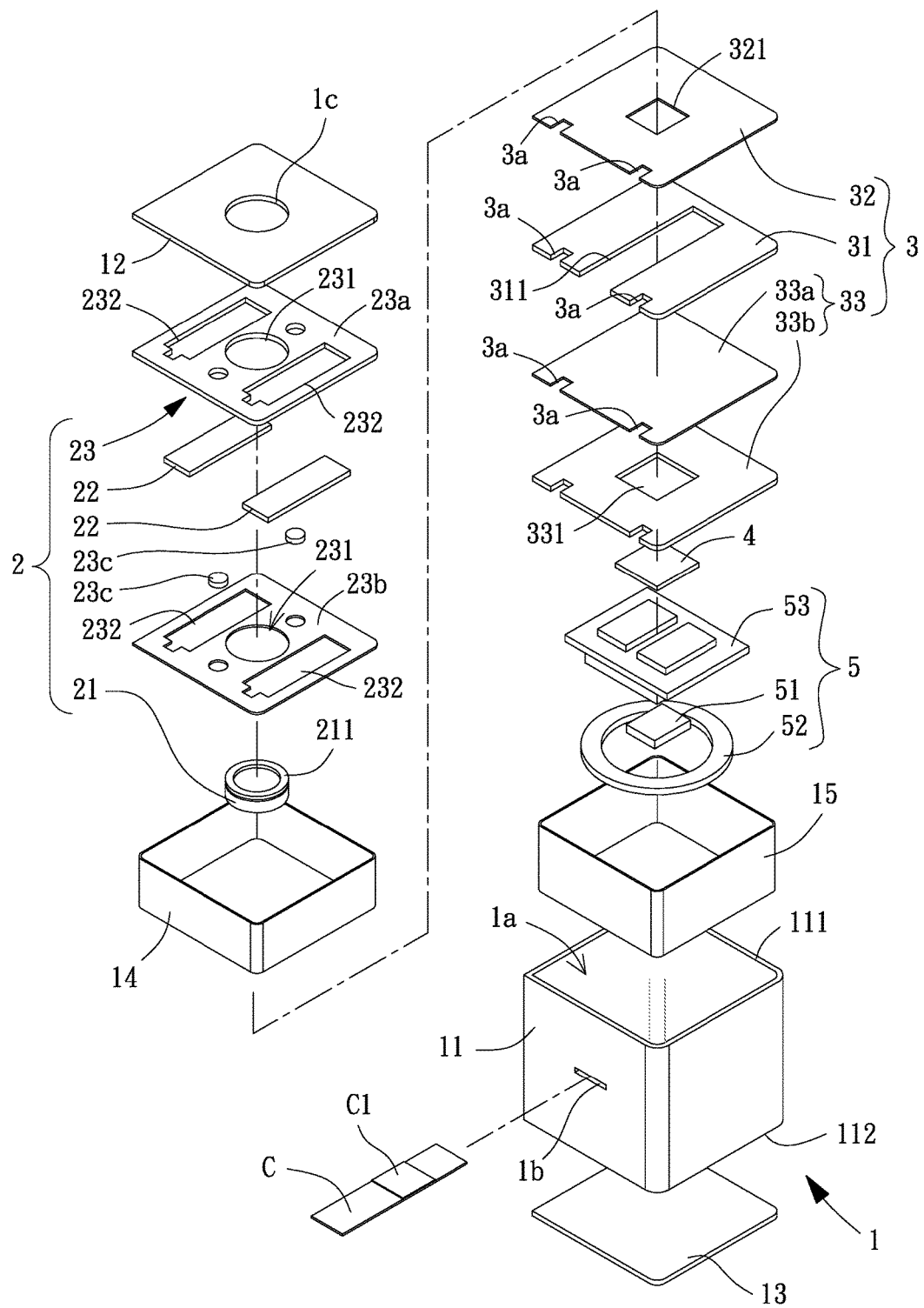
FIG. 1 is a perspective, exploded view of a biochip image-forming system according to an embodiment of the present invention.

In the various figures of the drawings, the same numerals designate the same or similar parts. Furthermore, when the terms "first", "second", "third", "fourth", "inner", "outer", "top", "bottom", "front", "rear" and similar terms are used hereinafter, it should be understood that these terms have reference only to the structure shown in the drawings as it would appear to a person viewing the drawings, and are utilized only to facilitate describing the invention.

DETAILED DESCRIPTION OF THE INVENTION

The term "coupling" used hereinafter in the specification of the present invention refers to coupling two electronic devices through electromagnetic coupling effect for conducting electricity or signals, but is not limited thereto. This definition can be readily appreciated by a person ordinarily skilled in the art.

FIG. 1 is a perspective, exploded view of a biochip image-forming system according to an embodiment of the present invention with a biochip. The biochip image-forming system can include a case 1, an optical assembly 2, a chip-holding assembly 3, a heating component 4 and an electricity storage assembly 5. The case 1 is adapted to receive the optical assembly 2, the chip-holding assembly 3, the heating component 4 and the electricity storage assembly 5. The chip-holding assembly 3 can be arranged between the optical assembly 2 and the heating component 4, and the electricity storage assembly 5 can be electrically connected with the optical assembly 2 and the heating component 4.

With references to FIG. 1, the case 1 can be made of a plastic material. A cavity 1a can be formed inside the case 1 for receiving the optical assembly 2, the chip-holding assembly 3, the heating component 4 and the electricity storage assembly 5. The cavity 1a can communicate with a chip inlet 1b and an image outlet 1c, with the chip inlet 1b adapted for a biochip "C" to be inserted into the cavity 1a through the chip inlet 1b, and with the image outlet 1c adapted for an image of the biochip "C" to be outputted from the cavity 1a through the image outlet 1c. In this embodiment, the case 1 can include a lateral wall 11 and two lids 12 and 13. The lateral wall 11 can include two opposite openings 111 and 112 communicating with the cavity 1a. The chip inlet 1b can be arranged in the lateral wall 11 between the two openings 111 and 112, and the image outlet 1c can be arranged in one of the lids 12 and 13. The two lids 12 and 13 can respectively cover the two openings 111 and 112, with the lid 12 having the image outlet 1c combined with the optical assembly 2, and with the other lid 13 combined with the electricity storage assembly 5. However, the present invention is not limited to the above. Besides, the case 1 can include a first supporting member 14 and a second supporting member 15. The first supporting member 14 can be arranged between the optical assembly 2 and the chip-holding assembly 3. The second supporting member 15 can be arranged between the chip-holding assembly 3 and the other lid 13. Each of the first and second supporting members 14 and 15 can be in the form of a frame, such as a rectangular or circular frame. The first and second supporting members 14 and 15 can be covered by an opaque material, such that the image of the biochip will not be affected by external light.

Still referring to FIG. 1, the optical assembly 2 can be composed of optical components having image-forming functions. The optical assembly 2 is received in the cavity 1a of the case 1. For instance, the optical assembly 2 can be fastened, engaged or press-fitted on an inner surface of the case 1. The optical assembly 2 is aligned with the image outlet 1c of the case 1 for outputting the image of the biochip "C." In this embodiment, the optical assembly 2 can include a lens assembly 21 and a backlight component 22, with the lens assembly 21 arranged between the image outlet 1c and the chip-holding assembly 3. The backlight component 22 can be fitted around the lens assembly 21 for emitting light towards the chip-holding assembly 3, forming the image of the biochip "C" via the lens assembly 21. The lens assembly 21 can include a set of convex lenses for magnifying the image of the biochip "C." The convex lenses set can have a magnifying power of 2× to 4× and a focal length of 1-2 cm, but is not limited thereto. Furthermore, the optical assembly 2 can include a base 23 having a lens-combining portion 231 and a backlight-positioning portion 232. The lens-combining portion 231 can be combined with the lens assembly 21, and the backlight component 22 can be arranged on the backlight-positioning portion 232. The base 23 can include an upper part 23a and a lower part 23b for conveniently combining with the lens assembly 21 and the backlight component 22. The upper and lower parts 23a and 23b can be stacked together. For instance, the upper and lower parts 23a and 23b can be made of paramagnetic materials, and a magnet set 23c can be arranged between the upper and lower parts 23a and 23b. In this way, the upper and lower parts 23a and 23b can be attracted by the magnet set 23c and combined together. The magnet set 23c can further attract and combine with other magnetic components for assembling the biochip image-forming system of this embodiment. The lens assembly 21 can also include a magnetic component 211 (e.g. a ring magnet), such that the lens assembly 21 can be combined with the lower part 23b via the magnetic component 211. Furthermore, the lower part 23b can be covered by an opaque material, such that the image formed via the lens assembly 21 is prevented from being affected by external light. However, it is not taken as a limited sense.

Still referring to FIG. 1, the chip-holding assembly 3 is received in the cavity 1a, such as being fastened, engaged or press-fitted to the inner surface of the case 1. The chip-holding assembly 3 can be arranged between the optical assembly 2 and the heating component 4. For instance, the heating component 4 can be a heating film. Alternatively, the heating component 4 can be a heating assembly including a temperature-controlling component and a heating film for temperature controlling purpose. Besides, the chip-holding assembly 3 aligns with the chip inlet 1b of the case 1 for the biochip "C" to be placed thereon. In this embodiment, the chip-holding assembly 3 can include a chip-guiding layer 31 having a groove 311 extending inwards from an edge of the chip-guiding layer 31. The groove 311 can align with or communicate with the chip inlet 1b of the case 1, such that the biochip "C" can be inserted and positioned in the groove 311 through the chip inlet 1b. Moreover, the chip-holding assembly 3 can include a shade layer 32 for shading external light. The shade layer 32 can be arranged between the chip-guiding layer 31 and the optical assembly 2, such as adhering on an upper surface of the chip-guiding layer 31 (with references to the orientation shown in the drawings). The shade layer 32 can include an observing window 321 aligned with the groove 311 of the chip-guiding layer 31. In this arrangement, the image of a reaction area C1 of the biochip "C" formed through the lens assembly 21 can be observed via the observing window 321. In addition, the chip-holding assembly 3 can include a heat-conducting member 33 arranged between the chip-guiding layer 31 and the electricity storage assembly 5. For instance, the heat-conducting member 33 can adhere on a lower surface of the chip-guiding layer 31 (with references to the orientation shown in the drawings). The heat-conducting member 33 can include a heater-combining portion 331 for combining with the heating component 4, such as a combining recess. As a further example, the heat-conducting member 33 can include a heat-conducting sheet 33a (e.g. a metal sheet) and a supporting sheet 33b (e.g. a thermosetting plastic sheet), with the heat-conducting sheet 33a arranged between the supporting sheet 33b and the chip-guiding layer 31 for enhancing the heat-conducting efficiency and structural strength of the heat-conducting member 33. The heater-combining portion 331 can be arranged on the supporting sheet 33b and aligns with the groove 311 of the chip-guiding layer 31. Through this arrangement, the biochip "C" can be efficiently heated by the heating component 4, advantageously affecting the reaction occurred in the reaction area C1 of the biochip "C." In order to heat the biochip "C" uniformly during the reaction process, the heat-conducting member 33 can be made of a material with high thermal conductivity, and the chip-guiding layer 31 can be made of a heat-resistant material. Besides, the chip-holding assembly 3 can include several penetrated portions 3a, such as through holes or tunnels, for a wire connected between the electricity storage assembly 5 and the optical assembly 2 to pass through the penetrated portions 3a. However, it is not taken as a limited sense.

Still referring to FIG. 1, the electricity storage assembly 5 can be electrically connected with the optical assembly 2 and the heating component 4 for supplying electricity to operate the optical assembly 2 and the heating component 4. In this embodiment, the electricity storage assembly 5 can include a rechargeable battery 51 (e.g. a Li-battery) and a wireless induction component 52 (e.g. a wireless induction coil or a wireless charging component). The rechargeable battery 51 can be electrically connected with the backlight component 22 of the optical assembly 2 and the heating component 4. The wireless induction component 52 can be coupled with the rechargeable battery 51 for charging the rechargeable battery 51 using an external power source or for switching on/off the electricity of the rechargeable battery 51. In the latter case, the wireless induction component 52 serves as an electric switch. However, as can be appreciated by persons having ordinary skilled in the art, a conventional switching component can also be used as the electric switch in the biochip image-forming system, which is not limited in the present invention. The electricity storage assembly 5 can further include a backlight-driving component 53 (e.g. a backlight voltage regulator) electrically connected with the rechargeable battery 51 and the backlight component 22 for supplying the required electricity to the backlight component 22. However, it is not taken as a limited sense.

Figure 2:
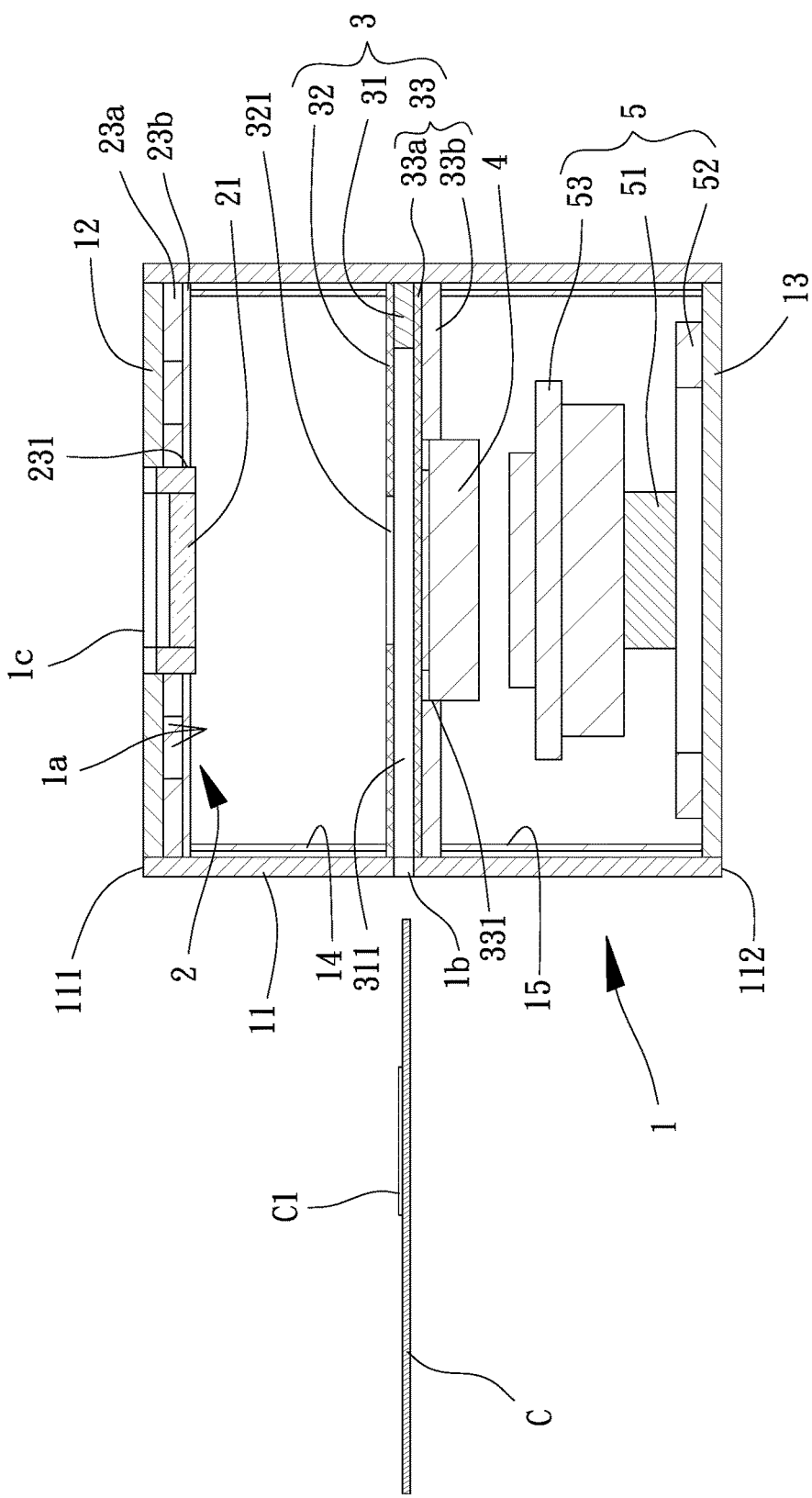
FIG. 2 is a cross sectional view of the biochip image-forming system according to the embodiment of the present invention.

Please refer to FIG. 2, which is a cross sectional view of the biochip image-forming system according to the embodiment of the present invention, with the biochip received therein. When assembling the biochip image-forming system, the rechargeable battery 51 of the electricity storage assembly 5 can be initially connected with the backlight component 22 of the optical assembly 2 and the heating component. Next, the lens assembly 21 of the optical assembly 2 and the backlight component 22 can be combined with the base 23 before combining the optical assembly 2 to the lid 12 of the case 1, with the lens assembly 21 of the optical assembly 2 aligned to the image outlet 1c of the case 1. The lid 12 can then be combined to the lateral wall 11 for covering the opening 111. After that, the first supporting member 14 can be placed in the cavity 1a inside the lateral wall 11, with a side of the first supporting member 14 contacting the base 23 of the optical assembly 2. Then, the chip-holding assembly 3 is placed in the cavity 1a inside the lateral wall 11, with the shade layer 32 contacting another side of the first supporting member 14. The groove 311 of the chip-guiding layer 31 communicates with the chip inlet 1b on the lateral wall 11, such that the biochip "C" can be inserted and positioned in the groove 311 through the chip inlet 1b. The second supporting member 15 can then be placed in the cavity 1a inside the lateral wall 11, with a side of the second supporting member 15 contacting the heat-conducting member 33 of the chip-holding assembly 3, followed by combining the heating component 4 to the heater-combining portion 331 of the heat-conducting member 33. Finally, the wireless induction component 52, the rechargeable battery 51 and the backlight-driving component 53 of the electricity storage assembly 5 can be sequentially stacked on the other lid 13 of the case 1, such that the lid 13 can be combined to the lateral wall 11 for covering the other opening 112. Through these processes, the biochip image-forming system of the present invention can be successfully assembled.

Figure 3:
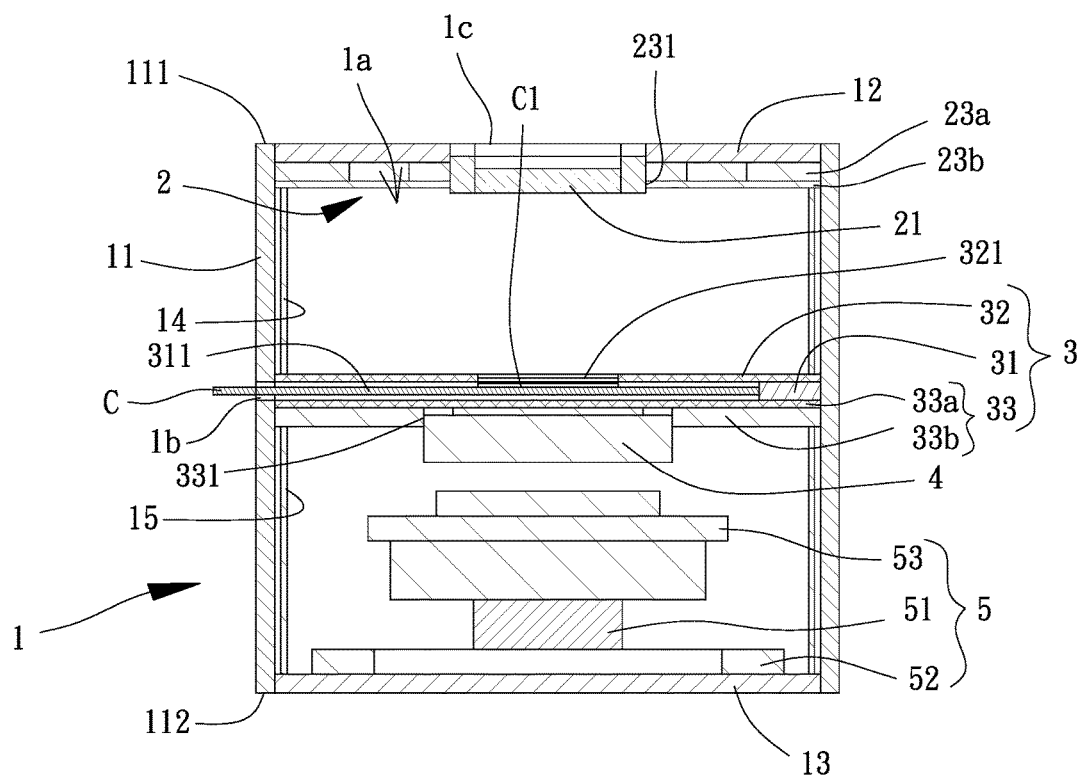
FIG. 3 illustrates the biochip image-forming system according to the embodiment of the present invention in use.

Please refer to FIG. 3, which illustrates the use of the biochip image-forming system according to the embodiment of the present invention with the biochip. When the biochip image-forming system is in use, the electricity storage assembly 5 supplies electricity to the heating component 4 and the backlight component 22 of the optical assembly 2. A user can prepare the biochip "C" for analysis and insert the biochip "C" in the groove 311 of the chip-holding assembly 3 through the chip inlet 1b. As an example, the biochip "C" for analysis can be prepare through dropping a biological specimen (e.g. a blood sample) on the reaction area C1 of the biochip "C." The heating component 4 can provide thermal energy to accelerate the reaction process, shortening the reaction time needed. Since the optical assembly 2 is provided, the user can observe the color in the reaction area C1 after the reaction. The result can be compared with corresponding references or databases, and can be analyzed manually or using corresponding devices.

According to the above disclosure, the biochip image-forming system of the present invention is characterized as follows. The cavity of the case communicates with the chip inlet and the image outlet, with the chip inlet adapted the biochip to be inserted into the cavity through the chip inlet, and with the image outlet adapted for the image of the biochip to be outputted from the cavity through the image outlet. The optical assembly aligns with the image outlet for forming the image of the biochip. The chip-holding assembly is arranged between the optical assembly and the heating component and aligns with the chip inlet for positioning the biochip. The electricity storage assembly is electrically connected with the optical assembly and the heating component. In this way, all these components of the biochip image-forming system described above can be and arranged within a single case, thus significantly reducing the volume of the biochip imaging-forming system and shortening the reaction time of the biochip.

According to the above, since the biochip image-forming system is provided with reduced volume and the reaction can be finished in a short time, the user can analyze the specimen collected on the biochip using the biochip image-forming system without the limitations of time and place. The biochip image-forming system meets the requirement for the patients to personally manage their disease progression, and overcomes the inconvenience due to particular time and place limitations of biochip analysis. Thus, the biochip image-forming system can be used in medical institutions and in home care.

Although the invention has been described in detail with reference to its presently preferable embodiments, it will be understood by one of ordinary skill in the art that various modifications can be made without departing from the spirit and the scope of the invention, as set forth in the appended claims.

What is claimed is:

1. A biochip image-forming system, comprising:
   a case having a cavity, wherein the cavity communicates with a chip inlet for a biochip to be inserted into the cavity through the chip inlet and an image outlet for an image of the biochip to be outputted from the cavity via the image outlet;
   an optical assembly received in the cavity and aligned with the image outlet for forming the image of the biochip;
   a chip-holding assembly received in the cavity and arranged between the optical assembly and a heating component, wherein the chip-holding assembly aligns with the chip inlet for the biochip to be placed thereon; and
   an electricity storage assembly electrically connected with the optical assembly and the heating component.

2. The biochip image-forming system as claimed in claim 1, wherein the optical assembly comprises a lens assembly arranged between the image outlet and the chip-holding assembly and a backlight component fitted around the lens assembly for emitting light towards the chip-holding assembly.

3. The biochip image-forming system as claimed in claim 2, wherein the lens assembly comprises a set of convex lenses having a magnifying power of 2× to 4× and a focal length of 1-2 cm.

4. The biochip image-forming system as claimed in claim 2, wherein the optical assembly comprises a base, and wherein the base comprises a lens-combining portion combined with the lens assembly and a backlight-positioning portion on which the backlight component is arranged.

5. The biochip image-forming system as claimed in claim 4, wherein the base comprises an upper part and a lower part stacked with each other.

6. The biochip image-forming system as claimed in claim 5, wherein a magnet set is arranged between the upper and lower parts.

7. The biochip image-forming system as claimed in claim 6, wherein the lens assembly comprises a magnetic member for combining the lens assembly to the lower part.

8. The biochip image-forming system as claimed in claim 5, wherein the lower part is covered by an opaque material.

9. The biochip image-forming system as claimed in claim 2, wherein the electricity storage assembly comprises a rechargeable battery and a wireless induction component, wherein the rechargeable battery is electrically connected with the backlight component and the heating component, and wherein the wireless induction component is coupled with the rechargeable battery.

10. The biochip image-forming system as claimed in claim 9, wherein the electricity storage assembly comprises a backlight-driving component electrically connected with the rechargeable battery and the backlight component.

11. The biochip image-forming system as claimed in claim 1, wherein the chip-holding assembly comprises a chip-guiding layer having a groove extending inwards from an edge of the chip-guiding layer, and wherein the groove aligns with the chip inlet of the case.

12. The biochip image-forming system as claimed in claim 11, wherein the chip-holding assembly comprises a shade layer arranged between the chip-guiding layer and the optical assembly, and wherein the shade layer comprises an observing window aligned with the groove of the chip-guiding layer.

13. The biochip image-forming system as claimed in claim 11, wherein the chip-holding assembly comprises a heat-conducting member arranged between the chip-guiding layer and the electricity storage assembly, and wherein the heat-conducting member comprises a heater-combining portion for combining with the heating component.

14. The biochip image-forming system as claimed in claim 13, wherein the heat-conducting member comprises a heat-conducting sheet and a supporting sheet, and wherein the heat-conducting sheet is arranged between the supporting sheet and the chip-guiding layer.

15. The biochip image-forming system as claimed in claim 13, wherein the heater-combining portion aligns with the groove of the chip-guiding layer.

16. The biochip image-forming system as claimed in claim 1, wherein the case comprises a lateral wall and two lids, wherein the lateral wall comprises two opposite openings communicated with the cavity, wherein the chip inlet is arranged in the lateral wall between the two openings, wherein the image outlet is arranged in one of the two lids, and wherein the two lids respectively cover the two openings.

17. The biochip image-forming system as claimed in claim 16, wherein the one of the two lids on which the image outlet is arranged is combined with the optical assembly, and wherein the other one of the two lids is combined with the electricity storage assembly.

18. The biochip image-forming system as claimed in claim 16, wherein the case comprises a first supporting member and a second supporting member, wherein the first supporting member is arranged between the optical assembly and the chip-holding assembly, and wherein the second supporting member is arranged between the chip-holding assembly and the other one of the two lids.

19. The biochip image-forming system as claimed in claim 18, wherein the first supporting member is in a form of a frame.

20. The biochip image-forming system as claimed in claim 18, wherein the first supporting member is covered by an opaque material.

* * * * *